US011534778B2

(12) United States Patent
Han et al.

(10) Patent No.: US 11,534,778 B2
(45) Date of Patent: Dec. 27, 2022

(54) DEVICE FOR PREPARING COSMETIC COMPOSITION CONTAINING EMULSION MATERIAL INSTANTLY EMULSIFIED BASED ON MICROFLUIDIC CHANNEL

(71) Applicant: AMOREPACIFIC CORPORATION, Seoul (KR)

(72) Inventors: Kyung Sup Han, Yongin-si (KR); Jin Nam, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 940 days.

(21) Appl. No.: 16/338,204

(22) PCT Filed: Sep. 29, 2017

(86) PCT No.: PCT/KR2017/011060
§ 371 (c)(1),
(2) Date: Apr. 19, 2019

(87) PCT Pub. No.: WO2018/062970
PCT Pub. Date: Apr. 5, 2018

(65) Prior Publication Data
US 2019/0336995 A1 Nov. 7, 2019

(30) Foreign Application Priority Data
Sep. 30, 2016 (KR) .................. 10-2016-0126312

(51) Int. Cl.
*B05B 7/04* (2006.01)
*A45D 34/00* (2006.01)
(Continued)

(52) U.S. Cl.
CPC ............... *B05B 7/04* (2013.01); *A45D 34/00* (2013.01); *A61K 8/064* (2013.01); *A61Q 19/00* (2013.01);
(Continued)

(58) Field of Classification Search
CPC ... B05B 7/04; B05B 11/0078; B05B 11/3081; B01F 23/41; B01F 2101/21; A45D 34/00; A45D 2200/056
See application file for complete search history.

(56) References Cited

U.S. PATENT DOCUMENTS 6,817,753 B2 * 11/2004 Buenger ................ B65D 83/68
222/145.5
9,655,431 B2 * 5/2017 Ham ...................... A45D 40/00
(Continued)

FOREIGN PATENT DOCUMENTS

CN 1343143 A 4/2002
CN 101380553 A 3/2009
(Continued)

OTHER PUBLICATIONS

English Abstract of Morinori Togashi, Micro-reactor applied to food industry, Jun. 30, 2009.
(Continued)

*Primary Examiner* — Jeremy Carroll
(74) *Attorney, Agent, or Firm* — Cantor Colburn LLP (57) ABSTRACT

An apparatus for preparing a cosmetic composition containing an emulsion substance formed by instant emulsification through a microfluidic channel is provided. The apparatus includes a housing defining the appearance of the apparatus and installed with a pump on one side, the pump being operated by a user; an external-phase chamber provided in the housing, and storing an external-phase fluid forming the external phase of the emulsion substance; a dispersed-phase chamber provided in the housing, and storing a dispersed-phase fluid forming the dispersed phase of the emulsion substance. The apparatus further includes a microfluidic channel providing a path for the external-phase fluid and the dispersed-phase fluid to flow for forming the emulsion substance by combining the external-phase fluid with the
(Continued)

dispersed-phase fluid; and a tube for discharging the emulsion substance from the microfluidic channel.

12 Claims, 5 Drawing Sheets

(51) Int. Cl.
    *B01F 23/41*     (2022.01)
    *B05B 11/00*     (2006.01)
    *B01F 101/21*     (2022.01)
    *A61K 8/06*     (2006.01)
    *A61Q 19/00*     (2006.01)

(52) U.S. Cl.
    CPC .......... *B01F 23/41* (2022.01); *B05B 11/0078* (2013.01); *B05B 11/3081* (2013.01); *A45D 2200/056* (2013.01); *B01F 2101/21* (2022.01)

(56) References Cited

U.S. PATENT DOCUMENTS

| | | | |
|---|---|---|---|
| 9,839,931 B2 * | 12/2017 | Burrowes | ........... B01F 25/4521 |
| 2003/0048693 A1 | 3/2003 | Buenger et al. | |
| 2006/0021996 A1 * | 2/2006 | Scott, III | ........... B65D 81/3283 |
| | | | 220/717 |
| 2016/0271576 A1 * | 9/2016 | Arab | ........ B01F 33/30 |
| 2016/0375413 A1 | 12/2016 | Weitz et al. | |
| 2020/0397696 A1 * | 12/2020 | Panagiotou | ......... B01F 35/2211 |
| 2021/0268454 A1 | 9/2021 | Weitz et al. | |

FOREIGN PATENT DOCUMENTS

| | | | |
|---|---|---|---|
| CN | 102574078 A | 7/2012 | |
| CN | 103764265 A | 4/2014 | |
| DE | 19911776 A1 | 9/2000 | |
| DE | 19911777 A1 | 9/2000 | |
| DE | 10333924 B3 | 10/2004 | |
| EP | 1810746 A1 | 7/2007 | |
| EP | 2033706 A2 | 3/2009 | |
| EP | 2033706 A2 * | 3/2009 | .......... B01F 13/0062 |
| EP | 2033706 B1 | 11/2012 | |
| EP | 2962751 A1 | 1/2016 | |
| JP | 2002538909 A | 11/2002 | |
| JP | 2009061382 A | 3/2009 | |
| KR | 1020100086779 A | 8/2010 | |
| KR | 1020150116485 A | 10/2015 | |
| WO | WO-2009120254 A1 * | 10/2009 | ......... B81C 1/00206 |
| WO | 2015160919 A1 | 10/2015 | |

OTHER PUBLICATIONS

English translation of Office Action dated Jun. 14, 2021, issued in Japanese Patent Application No. 2019-517424, 3 pp.
Morinori Togashi, Micro-reactor applied to food industry, Jun. 30, 2009, 59-65.
Office Action dated Jun. 14, 2021, issued in Japanese Patent Application No. 2019-517424, 3 pp.
English Abstract CN 103764265.
English Abstract DE 19911776.
English Abstract of CN 1343143.
English Abstract of DE 10333924.
English Abstract of DE 19911777.
Partial European Search Report for EP-Patent Application No. 17856856.4 dated May 14, 2020 corresponding to the above-referenced application.

* cited by examiner

DEVICE FOR PREPARING COSMETIC COMPOSITION CONTAINING EMULSION MATERIAL INSTANTLY EMULSIFIED BASED ON MICROFLUIDIC CHANNEL

This application is a national stage application of PCT/KR2017/011060, filed Sep. 29, 2017, which claims priority to KR 10-2016-0126312, filed Sep. 30, 2016, both/all of which are hereby incorporated by reference in their entirety.

TECHNICAL FIELD

The present disclosure relates to an apparatus for preparing a cosmetic composition containing an emulsion substance to dispense the emulsion substance formed by instant emulsification as one external-phase fluid and the other dispersed-phase fluid are made to flow through a microfluidic channel. In particular, the present disclosure relates to an apparatus for preparing a cosmetic composition containing an emulsion substance, for example, oil-in-water (O/W) emulsion particles or water-in-oil (W/O) emulsion particles, formed by instant emulsification readily when a user wants to use it by using properties of fluidic behaviors that fluids flow through a microfluidic channel.

BACKGROUND ART

In general, the fluid emulsification technology is for dispersing one of two immiscible fluids, for example, water and oil, as small particles, to disperse and dispose them in the other fluid to be stable. In the cosmetic industry, the emulsification technology is used widely to manufacture skin lotions, skin care creams, essences, massage creams, cleansing creams, makeup bases, foundations, eyeliners, mascaras, etc. That is, for manufacturing cosmetics listed above, small particles of a hydrophobic fluid like oil are dispersed homogeneously in a hydrophilic fluid like water to manufacture O/W or Oil-in-Water emulsion particles, or small particles of a hydrophilic fluid are dispersed homogeneously in a hydrophobic fluid to manufacture W/O or Water-in-Oil emulsion particles. The O/W emulsion particles and the W/O emulsion particles described above are referred to as an emulsion or emulsion substance.

For manufacturing such an emulsion substance, a physical method has been typically used to manufacture an emulsion substance by using a hydrophilic fluid and a hydrophobic fluid. For example, as disclosed in Korea Patent No. 10-0222000, a conventional method is to put both a hydrophilic fluid and a hydrophobic fluid in one large chamber and then use a mixer to disperse the particles of one fluid in the other fluid. For example, the mixer used for the purpose may be a homogenizer or microfluidizer. In other words, O/W emulsion particles or W/O emulsion particles are manufactured by putting a hydrophilic fluid and a hydrophobic fluid in a large chamber and then using a mixer to mix the fluids.

In the process described above, a surfactant is further added to the mixture to lower interfacial energy between the hydrophilic fluid and the hydrophobic fluid in order to form an emulsion substance readily, for example, the O/W emulsion particles or the W/O emulsion particles. It holds the interfacial membrane even harder to prevent the emulsion particles from being combined. Specifically, although an emulsion substance like the O/W emulsion particles or the W/O emulsion particles is formed by using a mixer, the emulsion particles are combined a given time after mixer operation stops, and the hydrophilic fluid and the hydrophobic fluid may thereby be separated from each other again. To avoid such a phenomenon, a surfactant is added to stabilize the small emulsified particles and keep the stable emulsion state for a long time.

A thickener is further added to the mixture to lower the emulsion substance mobility to avoid combination and separation of the emulsion substance, and enhance the thickness of a cosmetic product. The thickener added to the mixture ensures long-term stability of the cosmetic product, enhances thickness thereof, implementing better applicability thereof to the skin.

However, in the prior-art technology described above to manufacture a cosmetic composition containing an emulsion substance, it is required to form a large volume of the emulsion substance in advance to produce and sell a cosmetic composition product to meet user's needs. Therefore, it takes a long time to form the emulsion substance and then apply it as a cosmetic by users.

Furthermore, many restrictions are imposed inevitably in the process of manufacturing, packaging, and transportation of the emulsion substance in consideration of long-term stability to store a large volume of the emulsion substance product.

Although consumers further want cosmetics manufactured by minimizing the use of chemicals including surfactants and thickeners, the conventional cosmetics have been manufactured just in consideration of long-term storage of the products, and have never reflected customers' needs described above.

DISCLOSURE

Technical Problem

In view of the foregoing, the present disclosure provides an apparatus for preparing a cosmetic composition containing an emulsion substance formed by instant emulsification of the emulsion substance (or emulsion) such as O/W emulsion particles or W/O emulsion particles by using behavioral properties of fluids in a microfluidic channel, allowing users to use the emulsion substance product while forming the emulsion substance when they want to use it.

Technical Solution

In accordance with an aspect of the present disclosure, there is provided an apparatus for preparing a cosmetic composition containing an emulsion substance, the apparatus including: a housing defining the appearance of the apparatus and having a pump on one side, the pump being operated by a user; an external-phase chamber provided in the housing, and storing an external-phase fluid forming the external phase of the emulsion substance; a dispersed-phase chamber provided in the housing, and storing a dispersed-phase fluid forming the dispersed phase of the emulsion substance; a microfluidic channel providing a path for the external-phase fluid and the dispersed-phase fluid to flow for forming the emulsion substance by combining the external-phase fluid with the dispersed-phase fluid; and a tube for discharging the emulsion substance from the microfluidic channel.

In an embodiment of the apparatus, the microfluidic channel includes: an external-phase fluid delivery pipe for the external-phase fluid entering from the external-phase chamber to flow; a dispersed-phase fluid delivery pipe for the dispersed-phase fluid entering from the dispersed-phase chamber to flow; an intersection at which the external-phase fluid flowing through the external-phase fluid delivery pipe and the dispersed-phase fluid flowing through the dispersed-phase fluid delivery pipe meet each other as a point where the external-phase fluid delivery pipe communicates with the dispersed-phase fluid delivery pipe; and an emulsification part communicating with the intersection, and emulsifying the external-phase fluid and the dispersed-phase fluid to form the emulsion substance.

In an embodiment of the apparatus, the fluid channel further comprises an emulsion substance delivery pipe one end of which is connected to the intersection and the other end of which is connected to the end of the tube is formed downstream of the intersection to provide a path for the emulsion to flow, with respect to the fluid flow; and the emulsification part is installed upstream of the emulsion substance delivery pipe, with respect to the fluid flow.

In an embodiment of the apparatus, the emulsification part is an orifice smaller than the intersection in width.

In an embodiment of the apparatus, the emulsification part allows to: emulsify the external-phase fluid and the dispersed-phase fluid while the fluids are made to flow in the same direction; emulsify the external-phase fluid and the dispersed-phase fluid while they are made to flow to cross each other; emulsify the external-phase fluid and the dispersed-phase fluid by adjusting the aspect ratio of the external-phase fluid inlet to the dispersed-phase fluid inlet toward the intersection; form emulsion particles by making the dispersed-phase fluid, or the fluid mixture of the external-phase fluid and the dispersed-phase fluid flow through a membrane hole; form emulsion particles by using a power source generating at least one of an electric field, magnetic field, centrifugal force, laser and vibration; or form emulsion particles by changing fluid viscosity, interfacial tension or wetness levels.

In another embodiment of the apparatus, the emulsion substance is discharged by means of negative pressure generated by pump operation, and the tube is manufactured with a transparent material to allow its user to inspect it visually from the outside.

In yet another embodiment of the apparatus, the microfluidic channel has an internal wall with the property corresponding to the hydrophilicity of the external-phase fluid.

In an embodiment of the apparatus, the microfluidic channel is manufactured with a hydrophilic material for the hydrophilic fluid to flow toward the internal wall of the microfluidic channel where the external-phase fluid is a hydrophilic fluid.

In an embodiment of the apparatus, the water contact angle of the external-phase fluid against the internal wall of the fluid channel is in the range between 0 and 50 degrees; and the HLB value of a surfactant added to the emulsion substance is greater than 7.

In an embodiment of the apparatus, the microfluidic channel is manufactured with a hydrophobic material for the hydrophobic fluid to flow toward the internal wall of the microfluidic channel where the external-phase fluid is a hydrophobic fluid.

In an embodiment of the apparatus, the water contact angle of external-phase fluid against the internal wall of the microfluidic channel is in the range between 70 and 120 degrees; and the HLB value of a surfactant added to the emulsion substance is smaller than 7.

In yet another embodiment of the apparatus, one part of the fluid channel including the point where the external-phase fluid meets the dispersed-phase fluid has an internal wall with the property corresponding to the hydrophilicity of the external-phase fluid; the other part of the microfluidic channel positioned downstream of the one part of the microfluidic channel has an internal wall with the property corresponding to the hydrophilicity of the dispersed-phase fluid.

In yet another embodiment of the apparatus, the external-phase chamber and the dispersed-phase chamber are installed to be separated by a separating wall in the housing.

In yet another embodiment of the apparatus, the pump is one of a button-spring pump, syringe pump, tube pump, gear pump, porous pump, thread inserting pump, pump for sucking or discharging fluids by means of capillary action, and pump for sucking or discharging fluids by controlling electricity, vibration, sound waves, or piezoelectric materials.

Advantageous Effects

In accordance with the present disclosure, it is possible to form and dispense an emulsion substance while the emulsion substance (or emulsion) is formed by means of user's pump operation to allow users to form and dispense the emulsion substance when they want to use it.

Thus, since it is not necessary to store a large volume of the emulsion substance for a long time, many restrictions imposed for storage and transportation thereof in consideration of long-term stability of the emulsion substance product are not applied to the present disclosure any more.

Moreover, the present disclosure uses the behavioral properties of fluids that fluids flow through a microfluidic channel to form an emulsion substance readily, for example, the O/W emulsion particles or the W/O emulsion particles, formed by instant emulsification from the stored state of water- and oil-phase raw materials when users want to use the emulsion substance.

Further, in accordance with the present disclosure, since users may form and dispense an emulsion substance when they want to use it, their needs for minimized use of chemicals including surfactants and thickeners may be fully satisfied.

BEST MODE

The preferred embodiment of present disclosure will now be described with reference to the accompanying drawings. Although the present disclosure is described with reference to the embodiment depicted in the drawings, it should be noted that this is described just as an embodiment, and the technical idea of the present disclosure, key components and functions thereof are not limited thereto.

Figure 1:
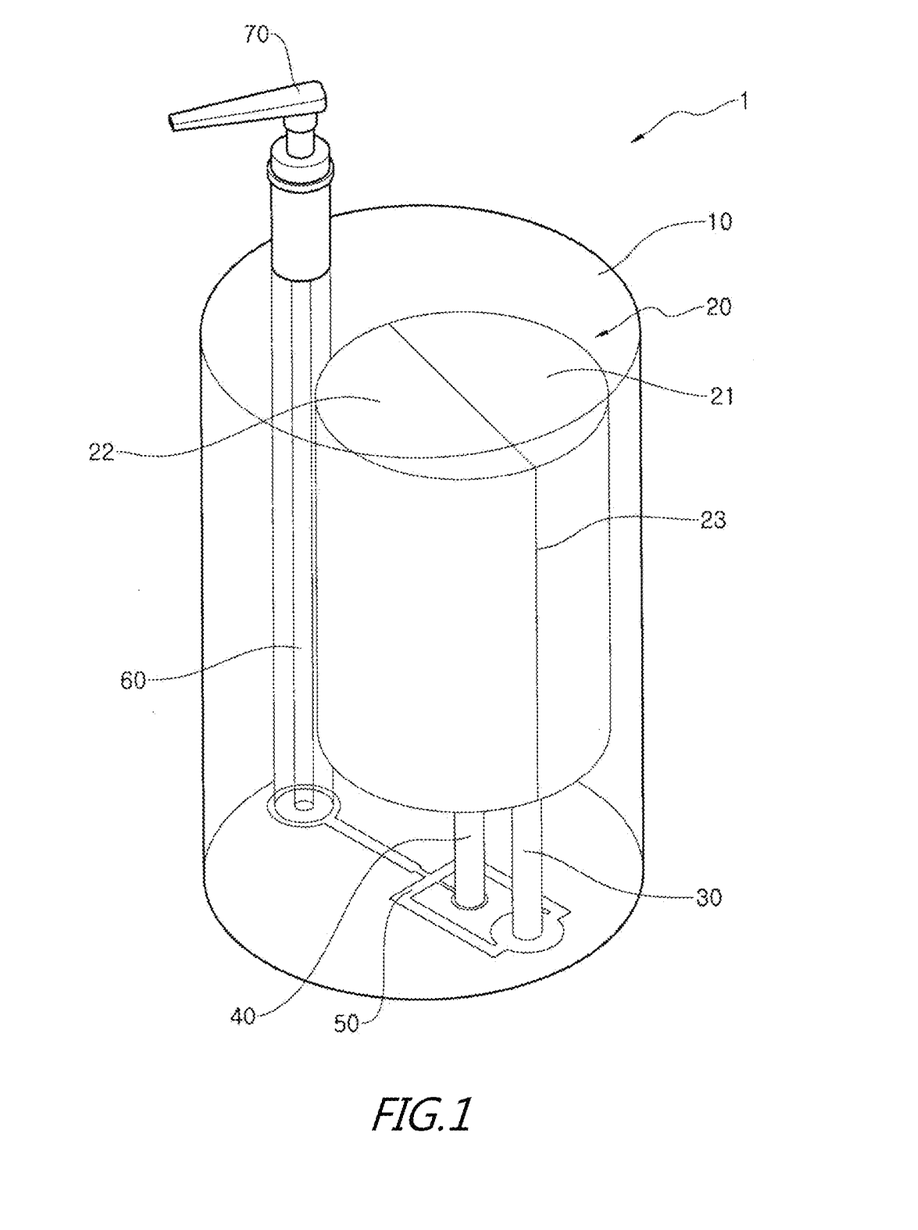
FIG. 1 is a perspective view of an apparatus for preparing a cosmetic composition containing an emulsion substance in accordance with an embodiment of the present disclosure.
Figure 2:
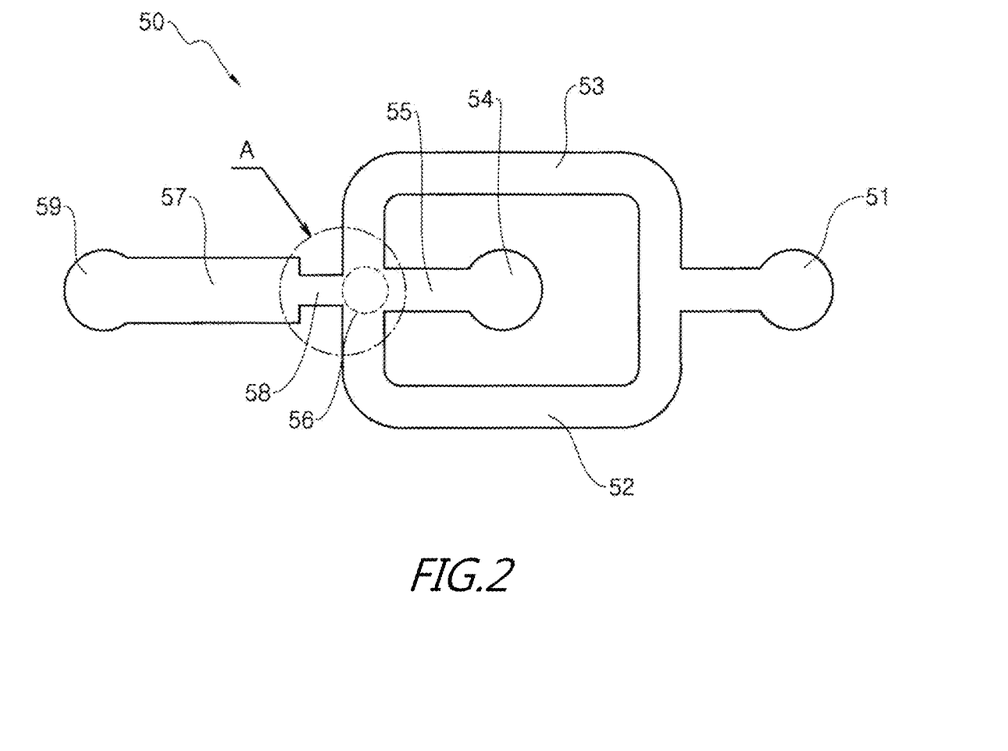
FIG. 2 is a top view showing the configuration of a microfluidic channel in the apparatus shown in FIG. 1.
Figure 3:
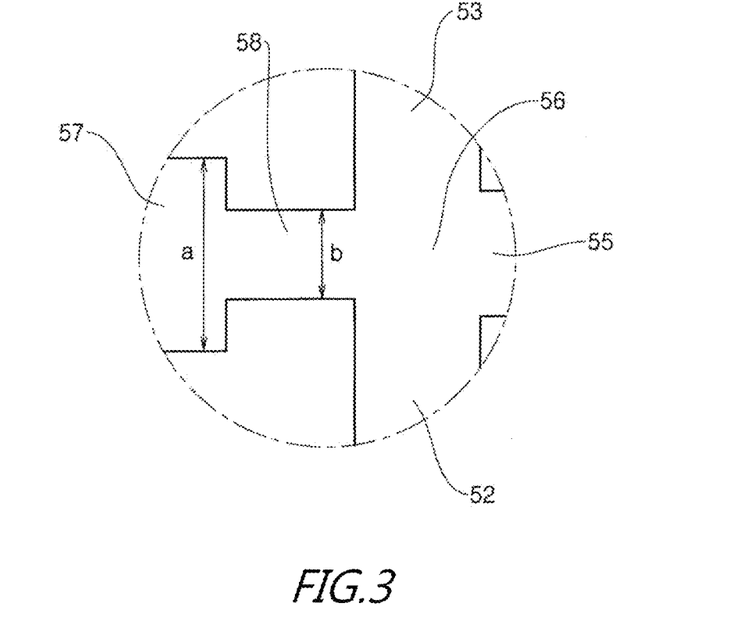
FIG. 3 is an expanded view of a portion of 'A' shown in FIG. 2.

FIG. 1 is a perspective view of an apparatus for preparing a cosmetic composition containing an emulsion substance in accordance with an embodiment of the present disclosure. FIG. 2 is a top view showing the configuration of the microfluidic channel in the apparatus shown in FIG. 1, and FIG. 3 is an expanded view of a portion of 'A' shown in FIG. 2.

Referring to the drawings, the appearance of the apparatus 1 for preparing a cosmetic composition in accordance with the present disclosure is formed with the housing 10. A pump 70 operated by its user is provided on one side of housing 10. The user may push down the pump 70 to dispense the material in the housing 10. For example, when the user pushes down the pump 70, the pressure given to the path for making the material in the housing 10 flow increases. In this state, when the user removes the hand from the pump 70 to release the pressure, negative pressure is given to the material delivery path to discharge the material.

The pump 70 is a means providing the energy for discharging and instantly emulsifying the fluids in the chambers 21 and 22, and dispensing the emulsified fluid mixture through the outlet formed on the outer side of the housing 10. The operation unit located on one side of the housing 10 and operated by the user may be exposed outside the housing 10, and the connection unit for discharging the fluid mixture may be provided in the housing 10. The pressure formed by the pump 70 makes the raw materials stored in the external-phase chamber 21 and the dispersed-phase chamber 22 provided to the microfluidic channel 50. The pressure also makes the raw materials provided to the microfluidic channel 50 flow through a given path and then flow into the pump 70 through the tube 60 after instant emulsification. For this purpose, flow channels communicating each other may be formed from the pump 70 to the respective chambers 21 and 22.

In this embodiment, although the configuration of the pump 70 is described to have an outlet exposed outside the housing 10 for discharging a cosmetic material, it should be noted that this is just as an example, and the idea of the present disclosure is not limited thereto. For example, the outlet may be a unit separated from the pump 70, and the pump 70 may be connected to any point in the flow channels connected from the chambers 21 and 22 to the outlet to give pressure.

The pump 70 described in this embodiment is an exemplary push-down pump for giving negative pressure to the path for making the fluids in the housing 10 flow while the user pushes down the pump and then removes the hand from the pump operation unit thereof to release the pressure. In this example, an advantage of this configuration is that the pressure given to just one direction formed by the pump 70 may make raw materials discharged from the chamber 21 and 22, flow through the microfluidic channel 50 and the cosmetic material dispensed to contribute to a simple configuration of the apparatus.

However, it should be noted that the idea of the present disclosure is not limited to the configuration, and any pump configured in different manners for the pump 70 may be used. For example, the pump 70 may be a manually operated pump, for example, the button-spring pump, syringe pump, tube or flexible tube pump, gear pump, porous pump, or thread inserting pump, or a pump for sucking or discharging fluids by means of the capillary action by applying an orifice, rollerball, or pencil to the outlet thereof. A motorized pump may otherwise be applied for controlling electricity, vibration, sound waves, or piezoelectric materials to suck or discharge fluids.

The housing 10 is provided with an external-phase chamber 21 for storing the external-phase fluid and a dispersed-phase chamber 22 for storing the dispersed-phase fluid. For example, the external-phase chamber 21 and the dispersed-phase chamber 22 may be provided in the housing 10 to be one fluid container 20. Specifically, a separating wall 23 extending from the top to the bottom and dividing the internal space of fluid container 20 is installed in the center of the fluid container 20. The external-phase fluid is stored on one side of the separating wall 23 to form the external-phase chamber 21, and the dispersed-phase fluid is stored on the other side thereof to form the dispersed-phase chamber 22.

The external-phase chamber 21 and the dispersed-phase chamber 22 are connected to the external-phase fluid injection tube 30 and the dispersed-phase fluid injection tube 40 used as the paths for the external-phase fluid and the dispersed-phase fluid stored therein to flow, respectively. In other words, the external-phase fluid stored in the external-phase chamber 21 may be discharged from the external-phase chamber 21 through the external-phase fluid injection tube 30. In a similar process, the dispersed-phase fluid stored in the dispersed-phase chamber 22 may be discharged from the dispersed-phase chamber 22 through the dispersed-phase fluid injection tube 40.

One end of the external-phase fluid injection tube 30 and one end of the dispersed-phase fluid injection tube 40 is connected respectively to the microfluidic channel 50. The microfluidic channel 50 may be formed as a passage to deliver fluids on the bottom of the housing 10. However, the installation location and shape of the microfluidic channel 50 are not limited to those described above.

With respect to the configuration, the connection of the chambers 21 and 22 to the injection tubes 30 and 40, respectively, may be provided with a switch to control opening and closing the connection, for example, a valve, to discharge the contents towards the injection tubes 30 and 40 only when pressure is given to the connection. In the present disclosure, the apparatus for preparing a cosmetic composition does not use a conventional syringe pump using positive pressure, but a microfluidic channel 50 using just negative pressure. That is, since the present disclosure uses just the negative pressure given to the microfluidic channel 50 to discharge the emulsion substance, it is an advantage that the apparatus in accordance with the present disclosure may be applied directly to the conventional cosmetic container and pump structures.

Conventionally, since great interfacial tension between the external-phase fluid and the dispersed-phase fluid contributes to the fluids not being mixed readily, an excessive amount of surfactants 1% to 5% is required to form and keep emulsion particles stable. However, since the effect of surface force on fluids in the microfluidic channel 50 in specific infinitesimal length or not greater than a millimeter in length is even greater than the body force, it is thus an advantage not to use a surfactant, or to minimize the amount of added surfactant to implement fast emulsification. Moreover, the principle that one fluid between two immiscible fluids breaks the flow of the other fluid to form emulsion particles helps to reduce the amount of required surfactants. Although the emulsification method using the microfluidic channel 50 has many advantages described above, the production speed is slower than the speed of conventional emulsifiers using a large tank and a mixer, and it is thus not an ideal option applied to cosmetic manufacturing apparatuses. To address such a production speed issue, the present disclosure develops a microfluidic channel 50 applicable to containers and employs an instant emulsification method for emulsification based on a predetermined amount of emulsion substance dispensed when a user wants to use it.

The microfluidic channel 50 may be formed with injection inlets communicating with the external-phase fluid injection tube 30 and the dispersed-phase fluid injection tube 40. In other words, the microfluidic channel 50 includes the external-phase fluid inlet 51 which is a passage for the external-phase fluid to flow through the external-phase fluid injection tube 30, and the dispersed-phase fluid inlet 54 which is a passage for the dispersed-phase fluid to flow through the dispersed-phase fluid injection tube 40.

The external-phase fluid flowing into the microfluidic channel 50 through the external-phase fluid inlet 51 may flow downstream toward the pump 70, and the microfluidic channel 50 is divided into the first branch pipe 52 and the second branch pipe 53. The term "downstream" as used herein refers to the direction in which the fluid stored in the fluid container 20 is discharged from the pump 70 through the microfluidic channel 50 and the tube 60 by means of user's pump operation. Since the first branch pipe 52 and the second branch pipe 53 provide a path for the external-phase fluid flowing in the microfluidic channel 50, it may be referred to as an external-phase fluid delivery pipe.

Similarly, the dispersed-phase fluid flowing into the microfluidic channel 50 through the dispersed-phase fluid inlet 54 may flow downstream through the dispersed-phase fluid delivery pipe 55. The external-phase fluid flowing through the external-phase fluid delivery pipe, that is, the first branch pipe 52 and the second branch pipe 53, meets the dispersed-phase fluid flowing through the dispersed-phase fluid delivery pipe 55 at the intersection 56. That is, the intersection 56 is the first point where the external-phase fluid meets the dispersed-phase fluid in the housing 10.

The external-phase fluid and the dispersed-phase fluid meeting at the intersection 56 pass through the emulsification part 58 to become an emulsion, that is, emulsion substance. The exemplary emulsification part 58 provided and described in this embodiment is an orifice 58 narrower than the intersection 56 in width. The external-phase fluid and the dispersed-phase fluid meeting at the intersection 56 pass through the orifice 58, and the external-phase fluid exerts shearing forces on the dispersed-phase fluid in the direction combining the forces in the narrower direction in the orifice 58 or the vertical direction (i.e., the diagonal direction toward the center of the orifice 58), and the fluid flow direction or the horizontal direction to break the entering dispersed-phase flow to form an emulsion substance. Specifically, when two immiscible fluids flow through the orifice 58 while their interface is unstable, capillary instability increases, and the channel with the orifice 58 may break the dispersed-phase fluid flow even with smaller energy in comparison with a channel without the orifice 58. The dispersed-phase fluid of broken flow is formed as spheres to remain stable.

The emulsification part 58 is used to enable the external-phase fluid to break the fluid mixture flow to disperse the fluid mixture as particles in the external-phase fluid, and it should be noted that the idea of the present disclosure is not limited thereto although the exemplary emulsification part 58 provided and described in this embodiment is an orifice. Specifically, the emulsification method using an orifice and employed in this embodiment is referred to as flow-focusing emulsification which is implemented by allowing fluids of different phases to flow in the same direction but placing an orifice at an intersection so that the external-phase fluid may break the dispersed-phase fluid flow. The orifice used as described above may divert the external-phase fluid flow into the diagonal direction in the orifice, and give stronger shear forces to the fluid mixture, thereby the emulsion particles being formed more readily while forming emulsion particles of similar size.

Furthermore, for the emulsification part 58, various embodiments may be applied as follows, and applicable examples include the method for emulsifying fluids of different phases while making them flow in the same direction, that is, Co-Flow method; the method for emulsifying fluids of different phases while making them flow to cross each other, that is, Cross-Flow method; the method for adjusting the aspect ratio of the inlets for the external-phase fluid and the dispersed-phase fluid led to the intersection to be great or small to form emulsion particles at the intersection, that is, Step Emulsification method; and the method for making the dispersed-phase fluid or a fluid mixture of two different phases flow through the hole of a membrane to form emulsion particles, that is, Membrane Emulsification method.

A power source may be used as the emulsification part 58, and an exemplary applicable channel for forming emulsion particles may be implemented by using an electric field or electrical control, magnetic field or magnetic control, centrifugal force or centrifugal control, lasers or optical control, vibrators or vibration control, piezoelectric materials, or piezoelectric control.

The emulsification part 58 may form emulsion particles by changing fluid viscosity, interfacial tension and wetness levels, and exemplary applications include electrorheological or ER, magnetorheological or MR fluids, or photosensitive fluids.

The emulsion substance formed while flowing through the orifice 58 flows into the tube 60 through the emulsion substance delivery pipe 57. For this purpose, an emulsion substance outlet 59 is formed at the end of the emulsion substance delivery pipe 57 to communicate with the tube 60 and functioning as a passage to allow the emulsion substance to flow out of the microfluidic channel 50.

The term "upstream" as used herein is used to refer to the direction opposite to "downstream", and means the direction opposite to the direction toward which the fluid flows by means of user's pump operation, that is, the direction towards the pump 70, tube 60, microfluidic channel 50 and fluid container 20.

In the prior-art technology, the size of emulsion substance has been controlled by controlling the amount of a surfactant added to the emulsion substance. However, in accordance with the present disclosure, it is possible to control the size of emulsion substance just by controlling the width of the orifice 58. However, the width of the orifice 58 has a predetermined minimum value, and the size of the emulsion substance thus has a lower limit.

In particular, in cosmetics manufactured by using an emulsifier, the size and contents of emulsion particles are an important factor determining the quality of cosmetics. In general, the ratio of the injected external-phase fluid must be equal to or higher than the ratio of the injected dispersed-phase fluid to form emulsion particles. For example, the amount of injected external-phase fluid may be in the range between the same and 30 times more than the amount of injected dispersed-phase fluid.

In a microfluidic channel 50 using just negative pressure as in the present disclosure, the speed of entering fluid is determined by the structural elements of the microfluidic channel 50 and fluid flow conditions, and the size and contents of emulsion particles thereby become different. Exemplary structural elements of the microfluidic channel 50 include channel height, orifice width, and respective channel width ratio for injecting fluids. Exemplary fluid flow conditions include negative pressure intensity, flow ratio of two fluids, and viscosity ratio of two fluids.

The emulsion particles become smaller where the channel height is lower; the orifice width is narrower; the negative pressure intensity is higher; the flow ratio of the external-phase fluid to the dispersed-phase fluid is greater; and the dispersed-phase fluid viscosity is greater than the external-phase fluid viscosity. They become larger in the opposite conditions.

In the present disclosure, the method for controlling the internal diameter of each inlet for the dispersed-phase fluid and the external-phase fluid is used to control the flow ratio of the dispersed-phase fluid to the external-phase fluid. Specifically, where the internal diameter of external-phase fluid injection inlet is twice as large as that of the dispersed-phase fluid injection inlet, the volume of flowing external-phase fluid is doubled in comparison with the dispersed-phase fluid flow just under negative pressure. In the same manner, the ratio of the dispersed-phase fluid flow to the external-phase fluid flow may be controlled. Moreover, to increase the contents of emulsion particles, it is required to make the flow ratio of two fluids the same if possible. However, where the dispersed-phase fluid flows faster than the external-phase fluid, the external-phase fluid does not have enough strength to break the dispersed-phase fluid flow, and it is thus hard to form emulsion particles.

In the present disclosure to address this issue, the ratio of the external-phase fluidic channel width to the dispersed-phase fluidic channel width may be controlled to control the speed at the intersection where the two fluids meet, and thus control the contents of emulsion particles although the flow ratio of two injected fluids is not controlled. For example, where the external-phase fluid channel width is made half the dispersed-phase fluid channel width, the speed of the external-phase fluid at the intersection where the two fluids meet may be twice as fast as the same width although the dispersed-phase fluid is injected twice as fast as the speed in same channel width. Therefore, the emulsion particles are formed as effective as where the external-phase fluid and the dispersed-phase fluid are injected in the same flow ratio, and the contents are doubled since the amount of injected dispersed-phase fluid is doubled.

The emulsion substance flowing through the emulsion substance delivery pipe 57 formed with the orifice 58 flows into the tube 60 through the emulsion substance outlet 59. The tube 60 may be made of a transparent material to allow the user to inspect the emulsion substance flowing through the tube 60. For this purpose, it may be also required to produce the area of the housing 10 surrounding the tube 60 with a material to allow the user to inspect the emulsion substance flowing through the tube 60 visually from the outside.

The pump 70 is installed at the end of the tube 60, and the user may dispense the emulsion substance from the outlet of the pump 70, flowing through the apparatus 1 for preparing a cosmetic composition.

The properties of material for manufacturing the microfluidic channel 50 may be different depending on the hydrophilicity of the external-phase fluid. The material for manufacturing the microfluidic channel 50 is described below.

Figure 4:
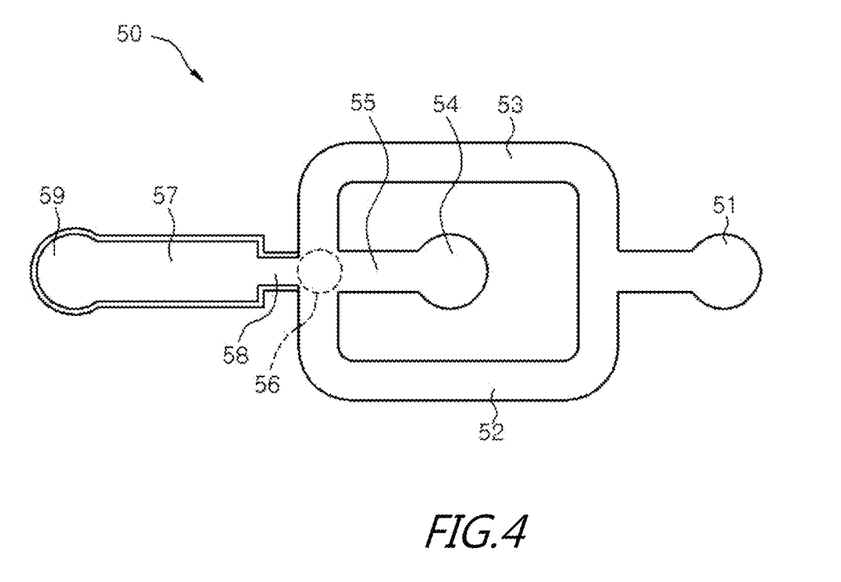
FIG. 4 shows an emulsion substance delivery pipe of the microfluidic channel, coated with a hydrophilic material.
Figure 5:
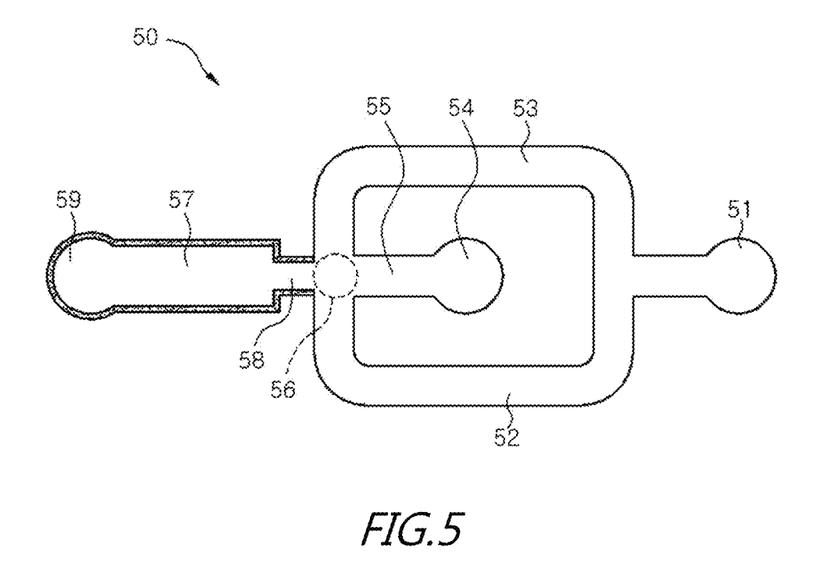
FIG. 5 shows an emulsion substance delivery pipe of the microfluidic channel, coated with a hydrophobic material.

FIG. 4 shows an emulsion substance delivery pipe of the microfluidic channel coated with a hydrophilic material. FIG. 5 shows an emulsion substance delivery pipe of the microfluidic channel coated with a hydrophobic material.

First, referring to FIG. 4, where the external-phase fluid in the external-phase chamber 21 is a hydrophilic fluid and the dispersed-phase fluid in the dispersed-phase chamber 22 is a hydrophobic fluid, the emulsion substance flowing through the microfluidic channel 50 becomes O/W emulsion particles.

For this process, it is preferred to manufacture the emulsion substance delivery pipe 57 with a hydrophilic material or the internal wall thereof contacting the fluid is coated with a hydrophilic material. Specifically, the emulsion substance has a configuration that the outer side thereof is made of the hydrophilic fluid and the hydrophobic fluid is dispersed therein. Therefore, where the emulsion substance delivery pipe 57 is manufactured with a hydrophilic material, the hydrophilic fluid in the emulsion substance is drawn to the wall of the emulsion substance delivery pipe 57. As a result, the O/W emulsion particles formed as described above effectively flow through the emulsion substance delivery pipe 57 while keeping their shape and structure.

Although it is described the emulsion substance delivery pipe 57 in this embodiment is manufactured with a hydrophilic material, the entire microfluidic channel 50 may be manufactured with a hydrophilic material for the manufacturing convenience purposes. Another applicable example is to manufacture just a part of the emulsion substance delivery pipe 57 with a hydrophilic material, provided that stable formation of the O/W emulsion particles is ensured. Furthermore, another applicable option is to coat the internal wall of the emulsion substance delivery pipe 57 with a hydrophilic material.

Where the emulsion substance delivery pipe 57 is hydrophilic, the water contact angle or WCA may be defined to be in the range between 0 and 50 degrees. With this setting, the O/W emulsion particles may flow more effectively.

As described above, where the emulsion substance delivery pipe 57 is manufactured with a hydrophilic material, the hydrophilic fluid in the emulsion substance is drawn to the wall of the emulsion substance delivery pipe 57. Therefore, the O/W emulsion particles may be formed stably. For more stable O/W emulsion particles, it is preferred to add a small amount of a surfactant of a high HLB (hydrophile-lipophile balance) or hydrophile-lipophile balance to the O/W emulsion particles. The HLB is an index illustrating the balance between hydrophilicity and hydrophobicity. It is preferred that the HLB of a surfactant added to the emulsion substance is greater than 7. That is, greater HLB values mean greater hydrophilicity. Where the value is greater than 7, preferably 8 to 16, it is easy to form the O/W emulsion particles.

For a conventional emulsifier, an important factor for forming emulsion particles is interfacial tension between the external-phase fluid and the dispersed-phase fluid. That is, in the prior-art technology, the phase of emulsion particles is determined depending on the HLB value of the surfactant, not on the hydrophilicity of the internal wall of channels or chambers.

However, in the present disclosure, the interfacial tension between the internal wall of the channels and the fluids is a very important factor for forming emulsion particles because of inwardly narrow channel width. That is, the hydrophilicity of the internal wall of the channel is an important factor for determining the phase of the emulsion particles, and a surfactant of an HLB value compatible with the phase of emulsion particles is then used to configure the entire emulsifier.

Meanwhile, as can be seen in FIG. 5, where the external-phase fluid in the external-phase chamber 21 is a hydrophobic fluid, and the dispersed-phase fluid in the dispersed-phase chamber 22 is a hydrophilic fluid, the emulsion substance flowing through the microfluidic channel 50 becomes the W/O emulsion particles.

For this process, it is preferred that the emulsion substance delivery pipe 57 is manufactured with a hydrophobic material or the internal wall of the delivery pipe is coated with a hydrophobic material. Specifically, since the emulsion substance has a configuration that the outer side thereof is made of the hydrophobic fluid and the hydrophilic fluid is dispersed therein, the hydrophobic fluid in the emulsion substance is drawn to the wall of the emulsion substance delivery pipe 57 where the emulsion substance delivery pipe 57 is manufactured with a hydrophobic material. Therefore, the W/O emulsion particles described above may effectively flow through the emulsion substance delivery pipe 57 while keeping their shape and structure.

Although it is described that the emulsion substance delivery pipe 57 is manufactured with a hydrophobic material in this embodiment, the entire microfluidic channel 50 may be manufactured with a hydrophobic material, or part of the emulsion substance delivery pipe 57 may be manufactured with a hydrophobic material for the convenient manufacturing purposes.

In this process, where the emulsion substance delivery pipe 57 is hydrophobic, the water contact angle or WCA may be set to be in the range 70 and 120 degrees. In this case, the W/O emulsion particles may flow more effectively.

As described above, where the emulsion substance delivery pipe 57 is manufactured with a hydrophobic material, the hydrophobic fluid in the emulsion substance is drawn to the wall of the emulsion substance delivery pipe 57. Therefore, the W/O emulsion particles may be formed stably. Moreover, for higher stability of the W/O emulsion particles, it is preferred to add a small amount of a surfactant of a low HLB to the W/O emulsion particles. Specifically, the HLB value of surfactant added to the emulsion substance is preferred to be smaller than 7. That is, greater HLB values mean greater hydrophobicity, and the value smaller than 7, preferably, 3 to 6, contributes to the W/O emulsion particles being formed effectively.

In general, the content of hydrophobic fluid which is a dispersed-phase fluid in the formed O/W emulsion particles is 0% to 30%. The hydrophobic fluid is injected into the microfluidic channel 50 through the dispersed-phase fluid inlet 54, and the hydrophilic fluid which is an external-phase fluid is injected into the microfluidic channel 50 through the external-phase fluid inlet 51.

In accordance with another example of the present disclosure alternative to the process described above, the content of the hydrophilic fluid which is a dispersed-phase fluid is 50% to 80% in the formed W/O emulsion particles. In this example, which is different from the O/W emulsion particles described above, the hydrophobic fluid which is an external-phase fluid may be injected into the dispersed-phase fluid inlet 54, and the hydrophilic fluid which is a dispersed-phase fluid may be injected into the external-phase fluid inlet 51 to increase the contents. That is, since the external-phase fluidic channel is divided into two branch pipes, the speed of forming emulsion particles is twice as fast as the case with just one channel. The reason for this benefit is as follows. That is, since the factor affecting formation of the emulsion particles the most in the microfluidic channel 50 is hydrophilicity of the internal wall of the channel or the internal wall of the emulsion substance delivery pipe 57, the hydrophilic fluid flows in the dispersed-phase while flowing through the emulsion substance delivery pipe 57 although the hydrophilic fluid is injected into the external-phase fluid inlet 51.

Figure 6A:
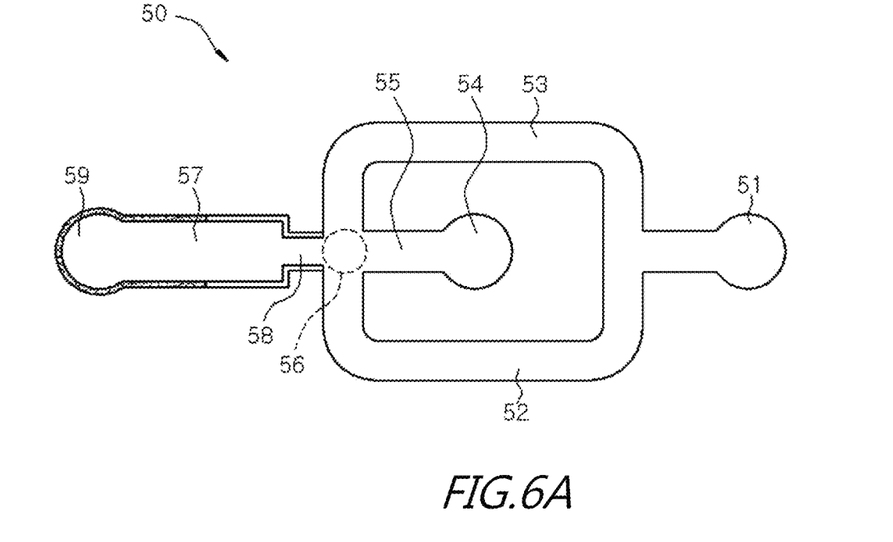
FIGS. 6A and 6B show another examples of the emulsion substance delivery pipe.
Figure 6B:
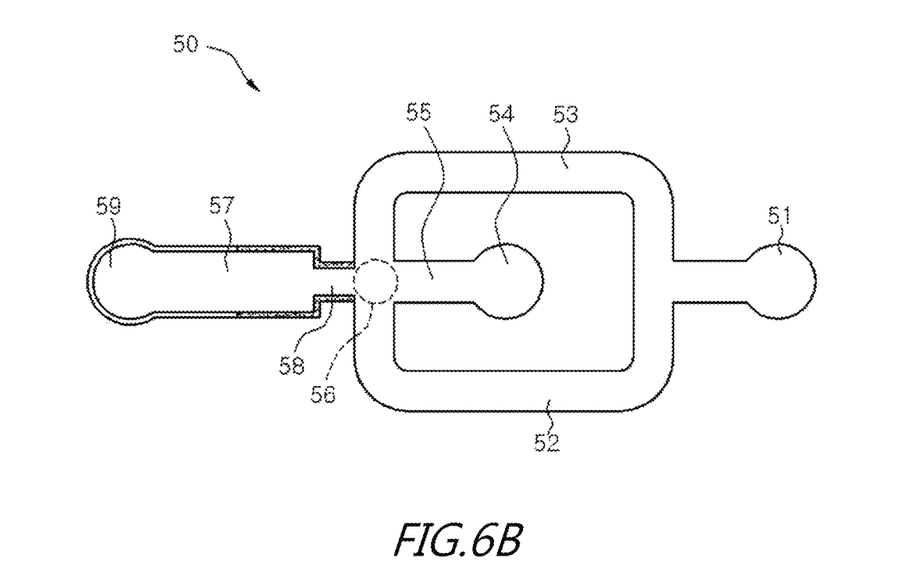

As another examples, FIG. 6 shows exemplary variants of the emulsion substance delivery pipe shown in FIG. 4.

As shown in FIG. 6A, the upstream area of the emulsion substance delivery pipe 57 may be manufactured with a hydrophilic material or the internal wall thereof coated with the hydrophilic material to form the O/W emulsion particles. The downstream area of the emulsion substance delivery pipe 57 may be manufactured with a hydrophobic material or the internal wall thereof coated with the hydrophobic material. For this purpose, the external-phase fluid is a hydrophilic fluid, and the dispersed-phase fluid is a hydrophobic fluid.

In accordance with this embodiment, the emulsion substance entering the emulsion substance delivery pipe 57 forms O/W emulsion particles in which the hydrophobic fluid is positioned in the hydrophilic fluid in the upstream area of the emulsion substance delivery pipe 57. The O/W emulsion particles stable in this state flow through the downstream area of the emulsion substance delivery pipe 57 of which the internal wall is manufactured or coated with a hydrophobic material. In this process, since the hydrophilic fluid is positioned on the internal wall of stable O/W emulsion particles, they contact the minimum area of the wall in the downstream area of the emulsion substance delivery pipe 57. Therefore, the stable O/W emulsion particles flowing through the upstream area of the emulsion substance delivery pipe 57 flow into the emulsion substance outlet 59 while being given with a minimum scale of friction force. As a result, the O/W emulsion particles may continue to keep the solid shape and structure thereof.

Similarly, referring to FIG. 6B, the upstream area of the emulsion substance delivery pipe 57 may be manufactured with a hydrophobic material or the internal wall thereof is coated with the hydrophobic material to form W/O emulsion particles. The downstream area of the emulsion substance delivery pipe 57 may be manufactured with a hydrophilic material or the internal wall thereof may be coated with the hydrophilic material. For this purpose, the external-phase fluid is a hydrophobic fluid, and the dispersed-phase fluid is a hydrophilic fluid.

In accordance with this embodiment, the emulsion substance entering the emulsion substance delivery pipe 57 forms the W/O emulsion particles in the upstream area of the emulsion substance delivery pipe 57. The stable W/O emulsion particles in this state flow through the downstream area of the emulsion substance delivery pipe 57 of which the internal wall is manufactured with or coated with a hydrophilic material. In this process, since the hydrophobic fluid is positioned on the internal wall of stable W/O emulsion particles, they contact the minimum area of the wall in the downstream area of the emulsion substance delivery pipe 57. Therefore, the stable W/O emulsion particles after flowing through the upstream area of the emulsion substance delivery pipe 57 flow into the emulsion substance outlet 59 while being given with a minimum friction force. As a result, the W/O emulsion particles may continue to keep the shape and structure thereof.

The fluid flow is described hereinafter in detail.

Figure 7:
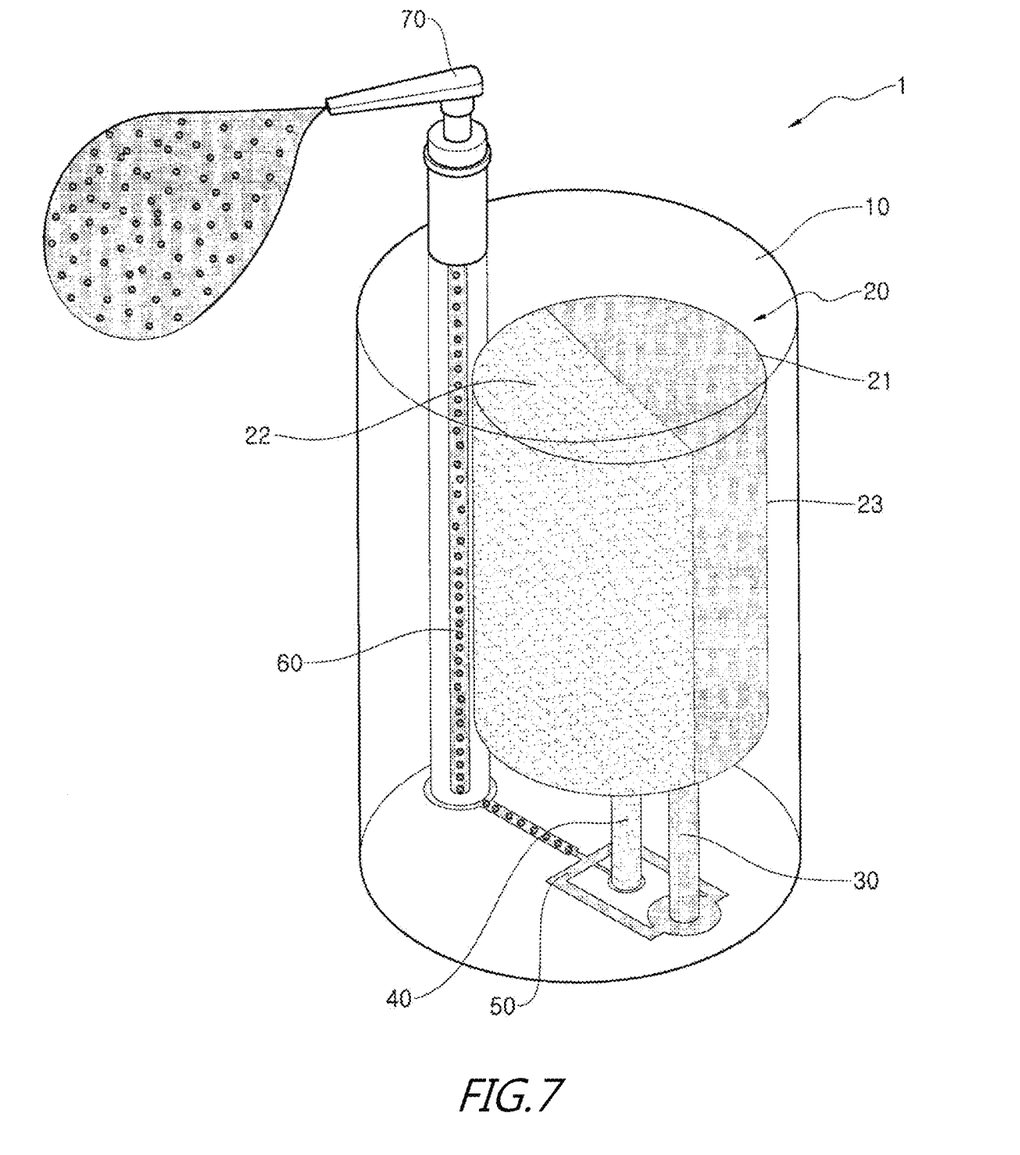
FIG. 7 is a perspective view showing a fluid flowing through the apparatus by means of user's pump operation.

FIG. 7 is a perspective view showing a fluid flowing through the apparatus by means of user's pump operation.

First, the process of discharging the O/W emulsion particles is described below.

To discharge the O/W emulsion particles, the external-phase fluid may be a hydrophilic fluid like water, and the dispersed-phase fluid may be a hydrophobic fluid like oil. The hydrophilic fluid and the hydrophobic fluid are stored in a different chamber, respectively. For example, the hydrophilic fluid is stored in the external-phase chamber 21, and the hydrophobic fluid is stored in the dispersed-phase chamber 22.

In this state, when the user pushes down the pump 70, the pressure given to the space for storing the fluids and the path for the fluids to flow in the housing 10 increases. Subsequently, when the user removes the hand from the pump 70 to release the pressure, negative pressure is given to the space for storing the fluids and the fluid delivery path to discharge the hydrophobic fluid and the hydrophilic fluid from the chambers, respectively.

Specifically, the hydrophilic fluid flows into the external-phase fluid inlet 51 of the microfluidic channel 50 through the external-phase fluid injection tube 30, and the hydrophobic fluid flows into the dispersed-phase fluid inlet 54 of the microfluidic channel 50 through the dispersed-phase fluid injection tube 40. The hydrophilic fluid entering the microfluidic channel 50 flows into the intersection 56 through the first branch pipe 52 and the second branch pipe 53. The hydrophobic fluid flows into the intersection 56 through the dispersed-phase fluid delivery pipe 55. That is, the hydrophilic fluid and the hydrophobic fluid meet at the intersection 56 of the microfluidic channel 50 each other.

The dispersed-phase fluid and the external-phase fluid are emulsified while flowing through the orifice 58, and the emulsion substance flowing through the orifice 58 flows through the emulsion substance delivery pipe 57. Since the emulsion substance formed in this process has a structure in which oil is dispersed in water, it is referred to as O/W or Oil in Water emulsion particles. That is, the emulsion substance is formed in such a form that the hydrophilic fluid surrounds the hydrophobic fluid.

Depending on the aforementioned process, the O/W emulsion particles flowing through the emulsion substance outlet 59 of the microfluidic channel 50 flow through the tube 60 and are discharged through the outlet of the pump 70 for the user.

In a similar process, the process of discharging the W/O emulsion particles is described herein below.

To discharge the W/O emulsion particles, the external-phase fluid may be a hydrophobic fluid like oil, and the dispersed-phase fluid may be a hydrophilic fluid like water. The hydrophobic fluid is stored in the external-phase chamber 21, and the hydrophilic fluid is stored in the dispersed-phase chamber 22.

In this state, when the user pushes down the pump 70 and then removes the hand from the pump 70, negative pressure is given to the space for storing the fluids and the path for the fluids to flow, and the hydrophobic fluid and the hydrophilic fluid are discharged from the chambers, respectively.

Specifically, the hydrophobic fluid flows into the external-phase fluid inlet 51 of the microfluidic channel 50 through the external-phase fluid injection tube 30, and the hydrophilic fluid flows into the dispersed-phase fluid inlet 54 of the microfluidic channel 50 through the dispersed-phase fluid injection tube 40. The hydrophobic fluid and the hydrophilic fluid entering the microfluidic channel 50 meet at the intersection 56 of the microfluidic channel 50 each other.

The dispersed-phase fluid and the external-phase fluid are emulsified while flowing through the orifice 58, and the emulsion substance flowing through the orifice 58 flows through the emulsion substance delivery pipe 57. Since the emulsion substance formed in the aforementioned process has the structure in which water is dispersed in oil, it is referred to as W/O or Water in Oil emulsion particles. That is, the emulsion substance is in a form that the hydrophobic fluid surrounds the hydrophilic fluid.

The W/O emulsion particles flowing through the emulsion substance outlet 59 of the microfluidic channel 50 in accordance with the aforementioned process flow through the tube 60 to be dispensed through the outlet of the pump 70 for the user.

As described above, while an emulsion substance (or emulsion) by means of user's pump operation is formed, the formed emulsion substance is dispensed in accordance with the present disclosure. Therefore, it is possible to form and dispense the emulsion substance when the user wants to use it.

Furthermore, since the emulsion substance is formed by combining the hydrophilic fluid with the hydrophobic fluid through instant emulsification in accordance with the present disclosure, the amount of a surfactant or thickener used for the emulsion substance may be minimized.

It should be noted that the explanation set forth above just illustrates the technical idea of the present disclosure, and those skilled in the art of the present disclosure may modify and change the idea of present disclosure in various ways within the scope not departing from the fundamental characteristics of the present disclosure. Therefore, the embodiment disclosed in the present disclosure is not intended to limit, but is intended to explain the technical idea of the present disclosure, and the scope of technical idea of the present disclosure is not limited by the embodiment. It should be noted that the scope of protection of the present disclosure is construed by the following claims, and all technical ideas within the scope equivalent thereto shall be construed to fall within the scope for the right of the present disclosure.

INDUSTRIAL APPLICABILITY

The present disclosure relates to an apparatus for preparing a cosmetic composition containing an emulsion substance formed by instant emulsification by using a microfluidic channel, and is applicable to the cosmetic industry.

The invention claimed is:
1. An apparatus for preparing a cosmetic composition containing an emulsion substance, the apparatus comprising:
  a housing defining the appearance of the apparatus;
  a pump being operated by a user;
  an external-phase chamber provided in the housing, and storing an external-phase fluid forming the external phase of the emulsion substance;
  a dispersed-phase chamber provided in the housing, and storing a dispersed-phase fluid forming the dispersed phase of the emulsion substance;
  a microfluidic channel providing a path for the external-phase fluid and the dispersed-phase fluid to flow for forming the emulsion substance by combining the external-phase fluid with the dispersed-phase fluid; and
  an outlet for discharging the emulsion substance from the microfluidic channel,
  the external-phase fluid stored in the external-phase chamber and the dispersed-phase fluid stored in the dispersed-phase chamber provided to the microfluidic channel, and then flow into the outlet after instant emulsification in the microfluidic channel by the pressure formed by operating of the pump by the user,
  wherein the microfluidic channel comprises:

an external-phase fluid delivery pipe for the external-phase fluid entering from the external-phase chamber to flow;

a dispersed-phase fluid delivery pipe for the dispersed-phase fluid entering from the dispersed-phase chamber to flow;

an intersection at which the external-phase fluid flowing through the external-phase fluid delivery pipe and the dispersed-phase fluid flowing through the dispersed-phase fluid delivery pipe meet each other as a point where the external-phase fluid delivery pipe communicates with the dispersed-phase fluid delivery pipe; and an emulsification part communicating with the intersection, which is narrower than the intersection in width, and emulsifying the external-phase fluid and the dispersed-phase fluid to form the emulsion substance, and wherein the emulsion substance is formed by forming emulsion particles by the external-phase fluid break entering dispersed-phase fluid flow in the emulsification part.

2. The apparatus of claim 1, wherein the fluid channel further comprises:

an emulsion substance delivery pipe (57) formed downstream of the intersection (56) to provide a path for the emulsion to flow to the outlet (59), with respect to the fluid flow; wherein the emulsification part (58) is installed upstream of the emulsion substance delivery pipe (57), with respect to the fluid flow.

3. The apparatus of claim 1, wherein the emulsification part (58) is an orifice smaller than the intersection (56) in width.

4. The apparatus of claim 1, further comprising a tube for discharging the emulsion substance from the microfluidic channel to the outlet, wherein the emulsion substance is discharged by means of negative pressure generated by pump operation, and the tube is manufactured with a transparent material to allow its user to inspect it visually from the outside.

5. The apparatus of claim 1, wherein the microfluidic channel has an internal wall with a property corresponding to a hydrophilicity of the external-phase fluid.

6. The apparatus of claim 5, wherein the microfluidic channel is manufactured with a hydrophilic material for the hydrophilic fluid to flow toward the internal wall of the microfluidic channel where the external-phase fluid is a hydrophilic fluid.

7. The apparatus of claim 6, wherein the water contact angle of the external-phase fluid against the internal wall of the fluid channel is in the range between 0 and 50 degrees; and the HLB value of a surfactant added to the emulsion substance is greater than 7.

8. The apparatus of claim 5, wherein the microfluidic channel is manufactured with a hydrophobic material for the hydrophobic fluid to flow toward the internal wall of the microfluidic channel where the external-phase fluid is a hydrophobic fluid.

9. The apparatus of claim 8, wherein the water contact angle of external-phase fluid against the internal wall of the microfluidic channel is in the range between 70 and 120 degrees; and the HLB value of a surfactant added to the emulsion substance is smaller than 7.

10. The apparatus of claim 1, wherein one part of the fluid channel comprising the point where the external-phase fluid meets the dispersed-phase fluid has an internal wall with a property corresponding to a hydrophilicity of the external-phase fluid;

the other part of the microfluidic channel positioned downstream of the one part of the microfluidic channel has an internal wall with a property corresponding to a hydrophilicity of the dispersed-phase fluid.

11. The apparatus of claim 1, wherein the external-phase chamber and the dispersed-phase chamber are installed to be separated by a separating wall in the housing.

12. The apparatus of claim 1, wherein the pump is one of a button-spring pump, syringe pump, tube pump, gear pump, porous pump, thread inserting pump, pump for sucking or discharging fluids by means of the capillary action, and pump for sucking or discharging fluids by controlling electricity, vibration, sound waves or piezoelectric materials.

* * * * *